United States Patent [19]

Kaufhold

[11] Patent Number: 4,851,552

[45] Date of Patent: Jul. 25, 1989

[54] PROCESS FOR THE PRODUCTION OF 13-OXABICYCLO(10.3.0)PENTADECANE AND PROCESS FOR THE PRODUCTION OF INTERMEDIATES

[75] Inventor: Manfred Kaufhold, Marl, Fed. Rep. of Germany

[73] Assignee: Huels Aktiengesellschaft, Marl, Fed. Rep. of Germany

[21] Appl. No.: 690,222

[22] Filed: Jan. 10, 1985

[30] Foreign Application Priority Data

Jan. 18, 1984 [DE] Fed. Rep. of Germany ....... 3400690

[51] Int. Cl.[4] .................. C07D 307/93; C07C 307/87
[52] U.S. Cl. .................... 549/462; 549/302; 558/371; 558/374; 562/510
[58] Field of Search ............. 549/302, 462; 558/371, 558/374; 562/510

[56] References Cited

U.S. PATENT DOCUMENTS 2,007,813  7/1935  Scheuing et al. .................. 549/302
4,222,904  9/1980  Meins et al. ....................... 549/462

OTHER PUBLICATIONS

DiBiase et al., J. Org. Chem., vol. 44(25), pp. 4640–4649 (1979).
Fieser and Fieser, Advanced Org. Chem., Reinhold Publ., pp. 365–366 (1961).
Modern Synthetic Reactions, Herbert O. House, W. A. Benjamin, Inc. Menlo Park, California (1972) pp. 649–650.

*Primary Examiner*—Henry R. Jiles
*Assistant Examiner*—Bernard I. Dentz
*Attorney, Agent, or Firm*—Millen & White

[57] ABSTRACT

13-oxabicyclo[10.3.0]pentadecane, a valuable ambergris fragrance, is prepared by reacting cyclododecanone with cyanoacetic acid in the presence of a Knoevenagel catalyst to form cyclododecenylacetonitrile, the nitrile is hydrolyzed to cyclododecenylacetic acid, and the acid is cyclized to the lactone, and the lactone is reduced to the corresponding diol which is cyclized to 13-oxabicyclo[10.3.0]pentadecane.

18 Claims, No Drawings

4,851,552

PROCESS FOR THE PRODUCTION OF 13-OXABICYCLO(10.3.0)PENTADECANE AND PROCESS FOR THE PRODUCTION OF INTERMEDIATES

BACKGROUND OF THE INVENTION

The invention relates to an improved process for the production of 13-oxabicyclo[10.3.0]pentadecane, a valuable ambergris fragrance with a very high fixative capacity. The following manufacturing method has been proposed in DOS No. 2,810,107:

1. Reformatskii reaction of cyclododecanone (I) with bromoacetic acid ester to obtain the corresponding hydroxy ester II.
2. Reaction of II with a strong acid to form the lactone III.
3. Reduction of III to the diol IV.
4. Cyclization with splitting of water in the presence of p-toluenesulfonic acid to obtain 13-oxabicyclo[10.3.0]pentadecane.

The bromoacetic acid ester utilized in this process is highly toxic and is an irritant to mucous membranes. Its use, therefore, required special safety measures. Additionally, the Reformatskii synthesis can be performed only by highly skilled personnel and is difficult to accomplish under industrial conditions.

The production of 13-oxabicyclo[10.3.0]pentadecane according to the process of DOS No. 3,040,994 proceeds via the following steps:

1. Bromination of cyclododecanone in the α-position with respect to the carbonyl group to obtain the bromoketone VI.
2. Reaction of α-bromocyclododecanone VI with the dialkyl ester of sodium malonic acid to obtain the dialkyl ester of 2-(2-oxocyclododec-1-yl)malonic acid VII.
3. Saponification with decarboxylation of VII to give the ketocarboxylic acid VIII.
4. Esterification of VIII with a low-boiling alcohol to obtain the corresponding ester IX.
5. Reduction of the keto ester IX with a metal hydride, such as NaBH$_4$, yields 2-(2-hydroxyethyl)cyclododecanol IV.
6. Cyclization of IV gives rise to V, as in the process of DOS No. 2,810,107.

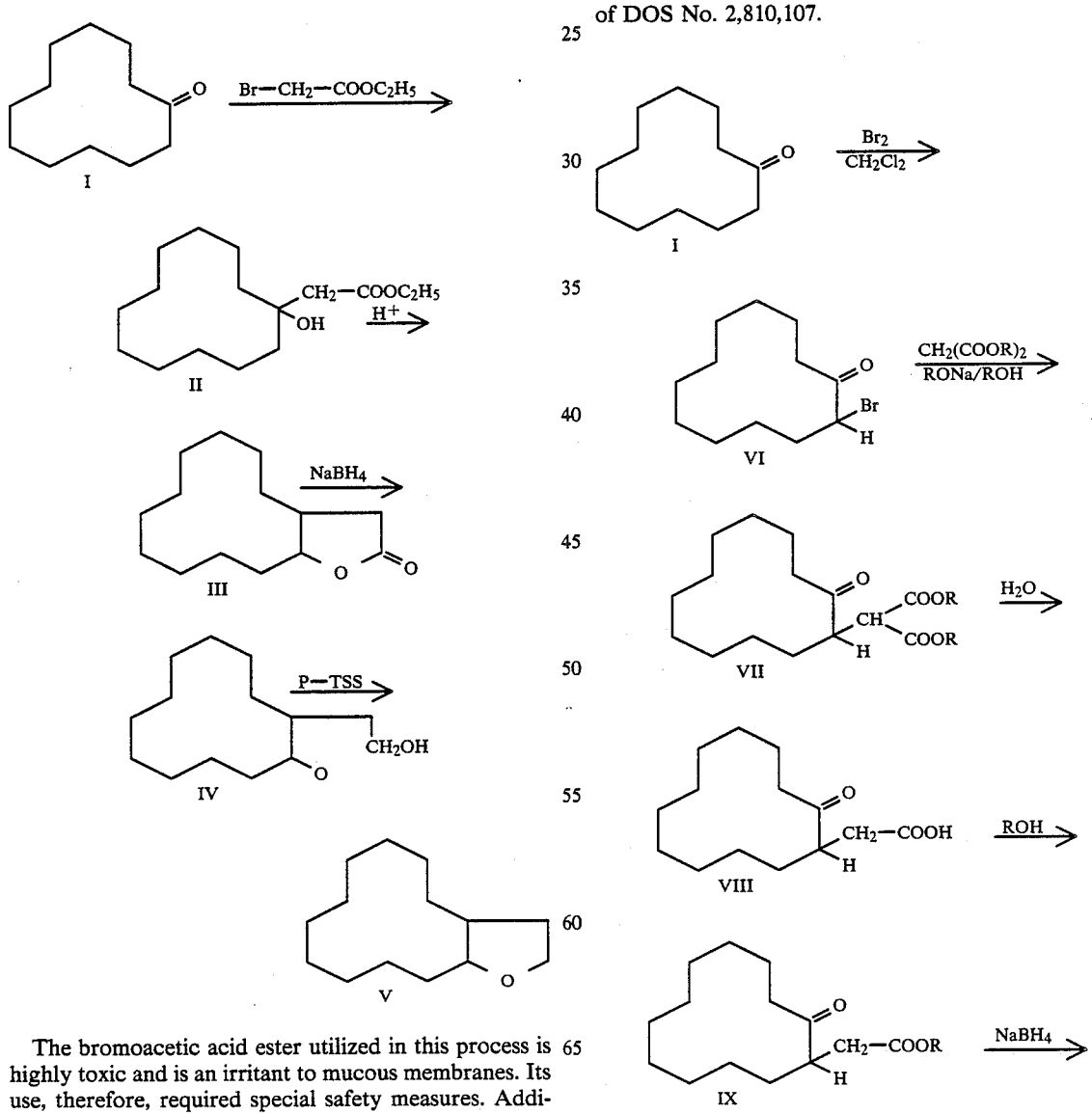

-continued

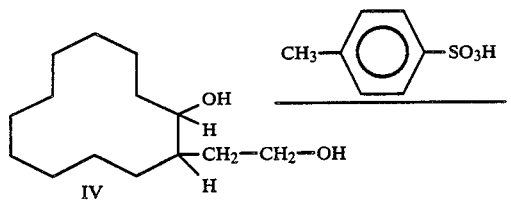

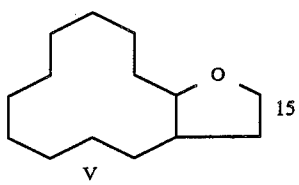

Even this improved manufacturing method still exhibits several drawbacks:

Bromine and sodium malonic acid dialkyl esters are expensive chemicals, and their use requires special industrial safety measures, such as, for example, complete exclusion of moisture during the reaction of the sodium compound. Moreover, only especially highly skilled personnel are permitted to handle highly toxic bromine and conduct the reaction of VI to VII which, according to DOS No. 3,040,994, requires "strictly controlled reaction conditions".

OBJECT OF THE INVENTION

It is an object of the present invention to provide a convenient and less costly process for making commercial quantities of 13-oxabicyclo[10.3.0]pentadecane using inexpensive chemicals which can be readily handled in conventional manufacturing equipment by personnel of average skill.

Upon further study of the specification and appended claims, further objects and advantages of this invention will become apparent to those skilled in the art.

SUMMARY OF THE INVENTION

These objects have been obtained by a process for the preparation of 13-oxabicyclo[10.3.0]pentadecane which comprises:

(a) reacting cyclododecanone with cyanoacetic acid in the presence of a Knoevenagel catalyst to form a nitrile, (b) hydrolyzing the nitrile to cyclododecenylacetic acid, (c) cyclizing the cyclododecenylacetic acid in the presence of a strong acid to the corresponding lactone, (d) reducing the lactone to the corresponding diol, and (e) cyclizing the diol in the presence of an acid to 13-oxabicyclo[10.3.0]pentadecane.

DETAILED DESCRIPTION

The first three steps of the above-described process are novel. Using that novel process, lactone III, 13-oxabicyclo[10.3.0]pentadecane-2-one is obtained in surprisingly high yields using procedures which are convenient to perform industrially.

Thus, using conventional equipment for chemical processing, very large quantities of 13-oxabicyclo[10.3.0]pentadecane can be manufactured without the need for special safety measures.

The novel process of the present invention starts with cyclododecanone and is performed as follows:

1. Cyclododecanone is reacted with cyanoacetic acid in the presence of a conventional Knoevenagel catalyst to obtain the cyclododecenylacetonitrile present as a mixture of isomers, X and XI.

2. Alkaline or acidic saponification of the nitrile X and XI (and subsequent acidification of the salt obtained during alkaline saponification) yields cyclododecenylacetic acid XII (cis and trans forms) and the isomeric acid XIII.

3. Heating of the mixture containing XII and XIII in the presence of a strong acid to obtain the lactone III.

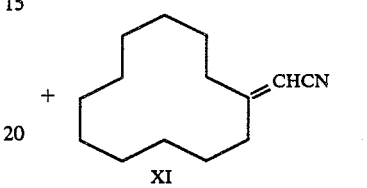

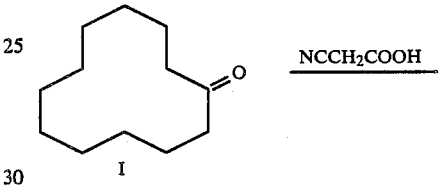

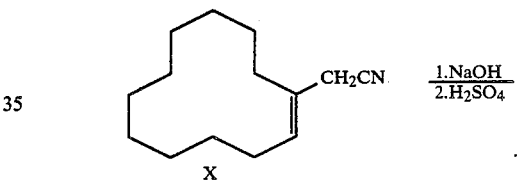

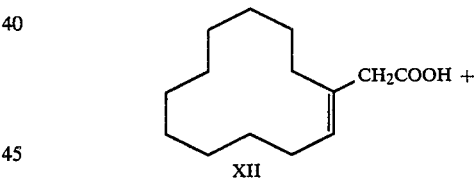

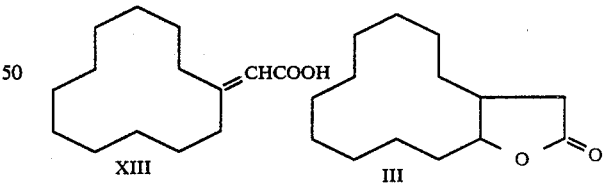

4. and 5. Reduction of the lactone III to the diol IV, catalytically, or by means of a borohydride such as NaBH$_4$, to give 2-(2-hydroxyethyl)cyclododecanol IV.

Cyclization of the diol with splitting off of water to obtain 13-oxabicyclo[10.3.0]pentadecane takes place according to the process of DOS No. 2,810,107.

Cyclododecenylacetonitrile, as a mixture of its cis and trans isomers, is obtained in an overall yield of more than 70% by the Knoevenagel reaction of cyclododecanone with cyanoacetic acid in the presence of a conventional Knoevenagel catalyst, such as ammonia or an amine, for example piperidine, β-alanine etc., preferably also in the presence of a carboxylic acid, for example, glacial acetic acid. Ammonium acetate is a preferred catalyst for the reaction because it is readily separable from the products of the reaction, it has the advantage of being very inexpensive, and does need not be recovered.

Organic chemistry textbooks state that good yields of product are obtained in the Knoevenagel reaction when short-chain ketones or carbonyl compounds activated by an aromatic ring are employed. In the aliphatic ketones series, e.g., acetone, butanone and cyclohexanone, the yields of product drop from 90% to 70%. In other words, the yield declines significantly as the chain length or number of carbon atoms increases, Organikum, 12th ed., VEB Deutscher Verlag der Wissenschaften, Berlin, 1973, page 508.

Thus, it could not be expected that the Knoevenagel reaction in a complex ring system having twice as many carbon atoms as cyclohexanone would give good yields of product. Nor, in contrast to a method described by Stephen A. DiBiase et al, Journal of Org. Chem., 44, No. 25, page 4640 (1979), could it be foreseen that a ketone with 12 carbon atoms reacts with a cyanoacetic acid in the presence of a very weak alkaline catalyst to produce more than a 70% yield of the corresponding substituted acetonitrile.

In practicing the process of the present invention, cyclododecanone is reacted with cyanoacetic acid in a molar ratio of 5:1 to 1:5, preferably 1:2 to 1:1, in the presence of 1–5% by weight, preferably 2–3% by weight of a conventional Knoevenagel catalyst based on cyclododecanone, at 100°–170° C. and preferably 120°–140° C. The reaction product is purified by distillation under vacuum, typically at 1–50 mbar. Cyclododecenylacetonitrile X, containing a small quantity of XI is obtained in a purity of above 99%.

Hydrolysis or saponification of the cyclododecenylacetonitrile containing mixture X and XI is conventional and can be effected with either acid or base. Alkaline saponification has the advantage that the work-up procedure is not complicated by the presence of ammonium salts. A suitable temperature range for the reaction is 100°–200° C., preferably 120°–180° C. The bases employed can be alkali or alkaline earth hydroxides, preferably an aqueous sodium hydroxide solution for ease of handling, utilized in a molar ratio of base:nitrile mixture of 10:1 to 1:1, preferably 2:1 to 1.05:1. Since solids precipitate during alkaline saponification, it is advantageous to add a solvent or solvent mixture, particularly if the process is to be carried out under atmospheric pressure and at temperatures that are not above 160°. Preferably, strongly polar, readily obtainable and inexpensive solvents are used, such as, for example, alkyl glycols, alkyl diglycols, alkyl polyglycols, the methyl, ethyl, propyl, or butyl group being especially suitable as the alkyl group, as well as ethylene glycol, diglycol, triglycol, polyglycol, or mixtures of these glycols and/or glycol derivatives, or the corresponding compounds derived from 1,2-propylene glycol. The progress of alkaline saponification can be determined by monitoring the ammonia liberated; the time required for saponification is generally from two to seven hours. Once evolution of ammonia has ceased, the reaction mixture is acidified with a mineral acid, preferably sulfuric acid, and extracted with an inert organic solvent. Especially suitable solvents for extraction are aromatic hydrocarbons, such as benzene, toluene, xylenes, and other alkyl benzenes, with toluene being preferred.

A particular advantage of the process of the present invention resides in the fact that the mixture containing XII and XIII need not be purified prior to further processing. In purifying the acid by distillation, considerable losses are incurred due to decomposition; purification by recrystallization would also result in loss of material and ultimately a lower yield of product.

It has been discovered surprisingly that cyclododecenylacetic acid, specifically the isomer mixture XII and XIII, reacts very smoothly with strong acids, such as mineral acids such as sulfuric acid, and p-toluene sulfonic cid, to yield lactone III. The reaction takes place generally at a temperature of between 40°–150° C. and preferably between 50°–100° C. This cyclization reaction is novel, and it could not be expected that the double bond present would show such great reactivity and that ring closure would be in the desired direction. Moreover, since XII is a $\beta,\gamma$-unsaturated carboxylic acid, and XIII is a substituted acrylic acid, considerable polymerization would have been expected under the drastic reaction conditions employed.

It is also surprising that the lactone III is obtained in a very pure form by distillation and has a sulfur content of less than 10 ppm, whereas its sulfur content prior to distillation was 50 ppm. Accordingly, in the subsequent reduction step, reduction with a relatively costly metal hydride, e.g. sodium borohydride (because of possible poisoning of the hydrogenation catalyst by sulfur) is not necessary as in the process of DOS No. 2,810,107, and the lactone III can be hydrogenated catalytically, preferably with a barium-activated copper chromite catalyst at temperatures of 150°–250° C. and under hydrogen pressures of 20–300 bar. Of course, reduction can also be effected with a borohydride.

The final step in the synthesis is identical with that in the process of DOS No. 2,810,107 (Example d). That patent also describes the special properties of 13-oxabicyclo[10.3.0]pentadecane and its use as a fragrance.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1.1 Synthesis of Cyclododecenylacetonitrile

In an agitated apparatus equipped with thermometer, reflux condenser and water trap, the following products are provided:

434 g (=5 moles) cyanoacetic acid
910 g (=5 moles) cyclododecanone
650 g toluene
21 g ammonium acetate This mixture is refluxed under agitation at 128°–130° C. under a nitrogen blanket for 30 hours, the thus-formed water, 80 g, being removed from circulation. During this step, a carbon dioxide stream is produced.

Weight of final product: 1,667 g.

This final product is distilled on a bridge arranged on a glass column having a length of 10 cm and filled with 10×10 mm glass Raschig rings; first of all, toluene, 480 g, is distilled off under normal pressure. In a boiling range of 120°–180° C. at 18–20 mbar, the nitrile mixture is then topped off from the residue, 89 g.

This distillation product, 996 g, is fractionated on a glass column having a length of 0.5 m and filled with multifil packing elements. At 13 mbar, 729 g of distillate is obtained in a boiling range of 170°–179° C.

The purity of the isomer mixture, determined by gas chromatography, is 99.1%; the contents of individual components were:

1st Component 63.2%
2nd Component 32.0%
3rd Component 3.9%

Components 1 and 2 are to be associated with structure X and are trans-cis isomers. The third component probably has structure XI.

The yield of X and XI is calculated to be 71.1%, based on the starting material.

1.2 Nitrile Saponification

In an agitated apparatus equipped with thermometer, reflux condenser and dropping funnel and traversed by a slight nitrogen stream passing, after the reflux condenser, through a washing receiver filled with 800 g of water, the following products are provided:

410 g (=2 moles) cyclododecenylacetonitrile mixture (99.6% strength)
40 g ethylene glycol
0.4 g tert-butyl pyrocatechol (as the stabilizer)

The mixture is heated to 154° C. under agitation. As listed in the overview table below, 50% strength sodium hydroxide solution, in total 240 g (=3 mol)=160 ml, and once 20 g of water and once 10 g of water are added. The table also shows the ammonia content in the washing water and the temperature data.

| Time (h) | Temp. (°C.) | Addition of Sodium Hydroxide Solution (ml) | Addition of Water (ml) | Ammonia Content (%) |
|---|---|---|---|---|
| Start | 154 | — | — | — |
| 0.5 | 134 | 30 | — | Not measured |
| 1.0 | 134 | 70 | — | " |
| 1.5 | 130 | 160 | 20 | 2.77 |
| 2.5 | 128 | — | — | 3.30 |
| 3.5 | 128 | — | 10 | 3.42 |
| 4.5 | 125 | — | — | 3.48 |
| 5.5 | 125 | | | 3.50 |
| 6.5 | 125 | | | 3.67 |

Then the mixture is cooled to about 100° C. and under agitation 400 g of toluene and 400 g of water are added. Thereafter, the mixture is cooled to room temperature and acidified with 738 g of 20% strength sulfuric acid to a pH of 3.0.

Phase separation yields:
1,381 g of aqueous phase and 825 g of oil phase.

The aqueous phase is extracted with 50 g of toluene. The carbon content of this wastewater then is 1.97%.

The oil phases are combined and the toluene is removed by distillation on a bridge arranged on an empty column having a length of 10 cm, initially at 200 mbar, then at 100 mbar, and finally at 20 mbar, at sump temperatures of respectively maximally 100° C.

Amount of distillate: 437 g
Amount of residue: 431 g

In accordance wwith the acid number of this residue (AN=215.1), the crude acid is of 85.9% strength. As based on this content and the starting material, the yield is calculated to be 82.6%.

1.3 Lactone Formation

The following material is charged into an agitated apparatus under a nitrogen blanket:

2,727 g (=22.3 mol) of sulfuric acid (80% strength).

The sulfuric acid is heated to 60° C. and, under vigorous agitation, the crude cyclododecenylacetic acid, 418 g (=1.6 mol), 85.9% strength, is added dropwise within 30 minutes. Then the mixture is stirred for another hour at 60° C.

In a second agitated apparatus, 2 liters of water cooled to 10° C. is provided and, under cooling, the reaction mixture is added within 2.5 hours in such a way that the temperature can be maintained at about 10° C.

Then the mixture is extracted first with 600 g of toluene and then with 300 g of toluene. Amount of wastewater: 4,741 g with contents of sulfuric acid of 45.8% and carbon of 0.79%.

The oil phases from the extraction, 991 g and 298 g, are combined and washed neutral with 150 g of a 10% soda solution. Amount of wastewater: 173 g.

The oil phase (1,258 g) is distilled on a glass column filled with multifil packing elements and having a length of 0.5 m, as follows:

| Fract. No. | Temperatures (°C.) Sump Head | Pressure (mbar) | Weight (g) | Ratio Reflux to Discharge |
|---|---|---|---|---|
| 1 | 116–170 87–110 | 1,013 | 805 | 3:1 |
|   | 96–198 37–46 | 13 |   | 10:1 |
| 2 | 214–222 131–194 | 13 | 43 | 5:1 |
| 3 | 222 194–202 | 13 | 9 | 5:1 |
|   |   |   |   | 30:1 |
| 4 | 222–252 202–209 | 13 | 270 | 30:1 |
|   |   |   |   | 3:1 |
|   | Residue |   | 13 |   |
|   | Cooling Trap |   | 77 |   |
|   |   |   | 1217 |   |

The cooling trap product is added to fraction 1 and the mixture is analyzed; it is pure toluene.

Fraction 2 consists of 97.2% cyclododecanone.

Fractions 3 and 4 are composed as follows, as per analysis by gas chromatography:

|  | Fract. No. 3 | Fract. No. 4 |
|---|---|---|
| First run | 2.7 | 0.1 |
| Cyclododecanone | 75.0 | 0.2 |
| Intermediate run | 1.7 |  |
| Component 1, b.p. about 365° C. | 14.5 | 62.9 |
| Component 2, b.p. about 365° C. | 1.7 | 31.1 |
| Component 3, b.p. about 365° C. | 0.3 | 5.2 |

Components 1, 2, and 3 concern the desired lactone.
The lactone yield is calculated from these data to be 75.3%, based on the crude acid employed.

The sulfur content of the lactone prior to distillation was 50 ppm and after distillation in the main run was only 6 ppm.

1.4.1 Reduction of the lactone is conducted with sodium borohydride in the same way as described in DOS No. 2,810,107, Example C: "The thus-obtained crude lactone (204 g) was dissolved in 3,600 ml of isopropanol. Under agitation, 45.6 g (1.2 mol) of sodium borohydride was added and the mixture was heated under reflux with agitation for 3 hours. After the reaction was completed, the mixture was poured into twice the quantity of water, extracted repeatedly with ether, the extracts dried, the solvent removed, and the crude product distilled under an oil pump vacuum.

The thus-produced diol represents a colorless, viscous liquid having a b.p.$_{0.6}$ of 172°–175° C."

1.4.2 Catalytic hydrogenation of the lactone takes place after dissolving in n-butanol in a ratio of 1:1 at 200° C. and under 30 bar of hydrogen pressure over a barium-activated copper chromite catalyst having the following composition: about 33% CuO, about 38% CrO$_3$, about 10% BaO, remainder SiO$_2$ (1,300 ml).

A 1.5-liter high-pressure reactor is utilized as the reaction vessel, and 250 ml/h of the solution is continuously added in metered amounts. The catalyst bed load is 0.096 l of lactone/l of catalyst.h.

The hydrogenation product has an acid number of 0.02 and a saponification number of 0.3, i.e. the lactone conversion is above 99%. After removing the butanol by distillation, the distillation residue is further processed directly.

1.5 The intramolecular water cleavage takes place in the same way as described in DOS No. 2,810,107, Example d: "The thus-obtained diol (208 g) was dissolved in 640 ml of toluene, 17.2 g of p-toluenesulfonic acid was added thereto, and the solution was heated for 2 hours on a water trap. After termination of the reaction, the mixture was washed neutral with 2N soda solution, thereafter with water, and the solution was dried over sodium sulfate. After removal of the solvent, the mixture was distilled in an oil pump vacuum."

13-Oxabicyclo[10.3.0]pentadecane is obtained as a mixture of isomers (concentrations of isomers: 75.7% and 23.2%) in 98.9% purity with good fragrance quality.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of 13-oxabicyclo[10.3.0]pentadecane which comprises:
   (a) reacting cyclododecanone with cyanoacetic acid in the presence of a Knoevenagel catalyst to form a nitrile,
   (b) hydrolyzing the nitrile to cyclododecenylacetic acid,
   (c) cyclizing the cyclododecenylacetic acid to the corresponding lactone,
   (d) reducing the lactone to the corresponding diol, and
   (e) cyclizing the diol in the presence of a strong acid to 13-oxabicyclo[10.3.0]pentadecane.

2. A process according to claim 1, wherein the Knoevenagel catalyst is ammonium acetate.

3. A process according to claim 1, wherein step (a) is effected at a temperature between 100°–170° C.

4. A process according to claim 1, wherein the nitrile is hydrolyzed in an alkaline solution in the presence of a polar solvent.

5. A process according to claim 1, wherein cyclododecenylacetic acid is cyclized by heating in the presence of a strong acid.

6. A process according to claim 5, wherein the strong acid is sulfuric acid.

7. A process according to claim 1, wherein the cyclododecenylacetic acid is not purified prior to lactone formation.

8. A process according to claim 1, wherein the lactone is reduced catalytically.

9. A process according to claim 8, wherein the catalyst is a barium-activated copper chromite catalyst.

10. A process for the preparation of cyclododecenylacetonitrile from cyclododecanone comprising:
    reacting cyclododecanone with cyanoacetic acid in the presence of aa Knoevenagel catalyst.

11. A process according to claim 10, wherein the Knoevenagel catalyst is ammonium acetate.

12. A process according to claim 10, wherein the reaction is effected at a temperature between 100°–170° C.

13. A process for the preparation of cyclododecenyl acetic acid which comprises:
    (a) reacting cyclododecanone with cyanoacetic acid in the present of a Knoevenogel catalyst to form a nitrile,
    (b) hydrolyzing the nitrile to cyclododecenylacetic acid.

14. A process according to claim 13, wherein the Knoevenagel catalyst is ammonium acetate.

15. A process according to claim 13, wherein step (a) is effected at a temperature between 100°–170° C.

16. A process according to claim 13, wherein the nitrile is hydrolyzed in an alkaline solution in the presence of polar solvent.

17. A process according to claim 13, wherein step (a) is effected at a temperature between 120°–140° C.

18. A process according to claim 16, wherein the alkaline solution is sodium hydroxide and the polar solvent is an alkyl glycol, an alkyl diglycol, an alkyl polyglycol, or a mixture of these glycols.

* * * * *